(12) United States Patent
Mückner et al.

(10) Patent No.: US 8,182,421 B2
(45) Date of Patent: May 22, 2012

(54) MEDICAL ENDOSCOPE WITH HEATED WINDOW

(75) Inventors: Andreas Mückner, Schwarzenbek (DE); Harald Lücht, Wentorf (DE)

(73) Assignee: Olympus Winter & IBE GmbH, Hamburg (DE)

( * ) Notice: Subject to any disclaimer, the term of this patent is extended or adjusted under 35 U.S.C. 154(b) by 667 days.

(21) Appl. No.: 12/416,572

(22) Filed: Apr. 1, 2009

(65) Prior Publication Data

US 2010/0010313 A1    Jan. 14, 2010

(30) Foreign Application Priority Data

Jul. 8, 2008  (DE) .......................... 102008031881

(51) Int. Cl.
*A61B 1/00* (2006.01)

(52) U.S. Cl. ........................................ 600/169; 600/129

(58) Field of Classification Search .................. 600/129, 600/130, 176, 169
See application file for complete search history.

(56) References Cited

U.S. PATENT DOCUMENTS

| 4,076,018 | A | | 2/1978 | Heckele |
| 4,182,547 | A | * | 1/1980 | Siegmund ...................... 385/117 |
| 5,009,655 | A | * | 4/1991 | Daignault, Jr. et al. ........... 606/7 |
| 5,605,532 | A | * | 2/1997 | Schermerhorn .............. 600/169 |
| 5,647,840 | A | * | 7/1997 | D'Amelio et al. ............. 600/169 |
| 5,992,728 | A | * | 11/1999 | Pollack et al. ............. 228/122.1 |
| 6,503,196 | B1 | * | 1/2003 | Kehr et al. .................... 600/176 |
| 2007/0149856 | A1 | | 6/2007 | Segawa |

* cited by examiner

*Primary Examiner* — John P Leubecker
(74) *Attorney, Agent, or Firm* — Rankin, Hill & Clark LLP

(57) ABSTRACT

A medical endoscope (1) fitted with an optics duct (4) receiving an optical system (9, 10) enclosed by a system tube (6), the distal end of the optics duct (4) being closed by a window (5) to the inner surface of which is mounted an electrical heater (11), characterized in that the heating ring (11) rests against the inner surface of the window (5) while being pressed in that direction by a spring (13).

3 Claims, 1 Drawing Sheet

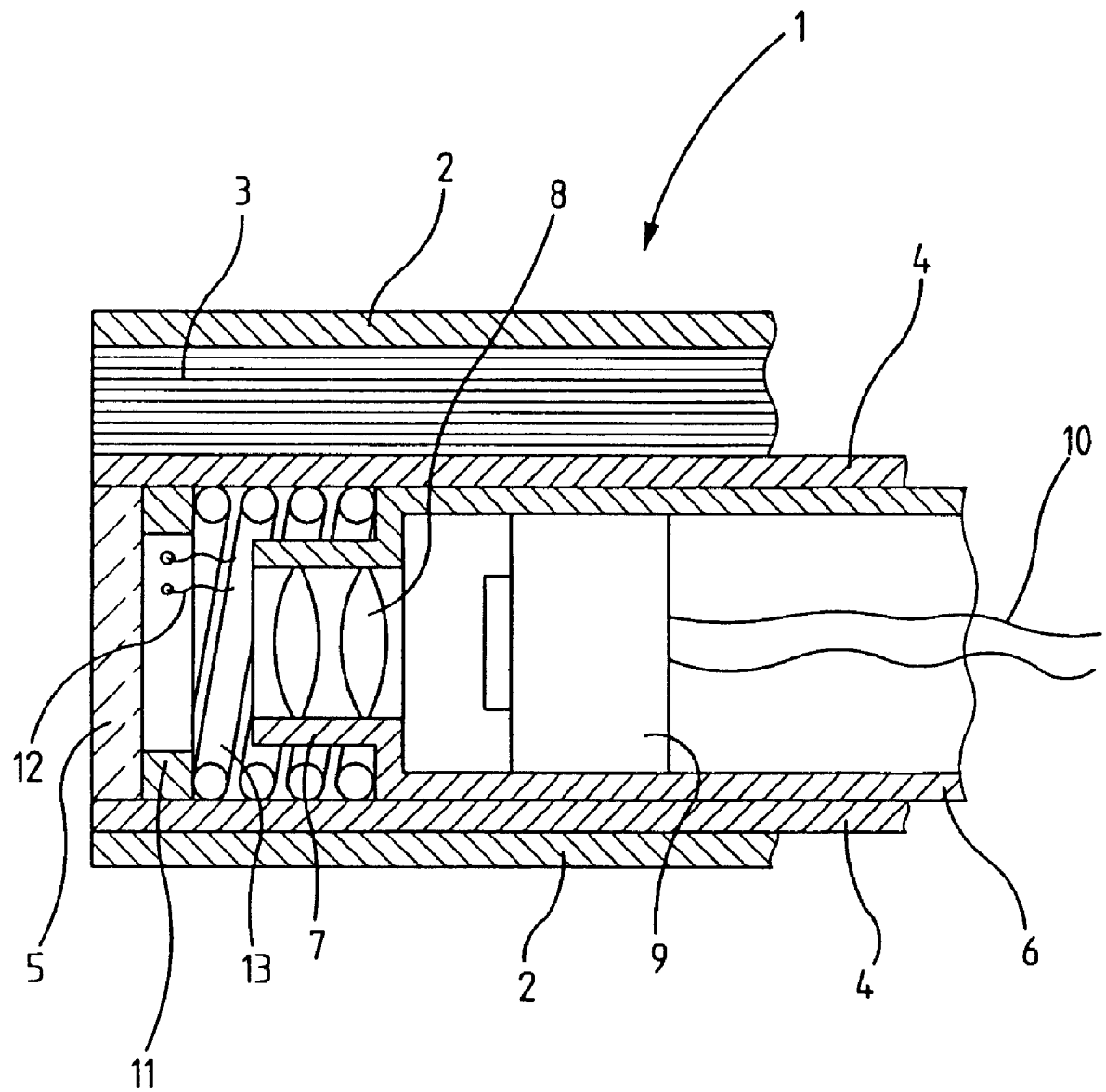

MEDICAL ENDOSCOPE WITH HEATED WINDOW

BACKGROUND OF THE INVENTION

1. Field of the Invention

The present invention relates to a medical endoscope having an optical system enclosed by a system tube, the distal end of the optics duct being sealed by a window fitted at its inner surface with an electrical heating ring.

2. Description of Related Art

When employed as designed for, medical endoscopes are inserted by their distal end into a body-warm and moist body cavity while initially being still at the lower outside temperature. Inevitably the distal window fogs up. The surgeon must wait until the fog on the window disappears on account of temperature balancing and gradual evaporation and must resort to the conventional remedial steps, illustratively wiping dry the fogged-up window near a body part.

A number of window heating systems are known in the state of the art using diverse heating means, among which is electric power.

Illustratively, electrical heating systems are known from the U.S. Pat. No. 4,076,018 in which electrical conductors are applied to the inner window surface.

The US patent document 2007/0149856 A1 of this kind discloses, moreover, a temperature sensor to control the heating power, a heating ring being used and configured in the region between the distal system tube receiving a video system and the window.

The present state of the art addresses inadequately the problem of affixing the heating ring. The first aforementioned literature mentions several ways, illustratively the heating conductor being applied internally or externally to the window or being fused in it. Also this literature proposes configuring said conductor around the window.

Problems arise when the heating ring is mounted at the window. Illustratively adequate thermal contact might be attained by fusing, bonding and the like of the heater into/at the window, however at the cost of raising assembly problems. On the other hand, should the heating ring be merely deposited, the thermal contact would be inadequate.

Accordingly it is the objective of the present invention to optimize the heating ring configuration in an endoscope of the aforementioned kind.

BRIEF SUMMARY OF THE INVENTION

In the present invention, the heating ring is spring-loaded to rest against the inner window surface. Accordingly, the contact is highly thermally conductive while devoid of cumbersome assembly procedures such as fusing, bonding, screwing or the like.

In order to apply an appropriate compression in the distal direction, said spring must be supported somewhere by the endoscope. Advantageously, the spring rests against the system tube. This tube terminates near the window and offers appropriate support to the window.

The heating ring, the spring and the system tube can be removed in the proximal direction from the optics duct, that is, they are axially displaceable within this duct. Assembly merely requires that the proximal system tube end be advanced somewhat farther while compressing the spring and then be secured in that position. In this design the spring not only may supply the heating-ring pressure, but also may eliminate the play for all elements consecutively stacked in the optics duct.

BRIEF DESCRIPTION OF THE DRAWINGS

The single FIG. 1 shows in an illustrative and schematic manner an axial section of the distal end zone of an endoscope of the present invention.

DETAILED DESCRIPTION OF THE INVENTION

FIG. 1 shows the distal end segment of a medical endoscope 1 which in this embodiment mode follows the conventional design and, by means of an outer tube 2, encloses a light guide fiber bundle 3 that is internally braced by a fiber tube 4 that is configured excentrically and subtends within it an optics duct.

The distal end of the optics duct constituted by the fiber tube 4 is sealed by a window 5 conventionally configured together with the distal ends of the tubes 2 and 4 and with the light guide fiber bundle 3 to subtend a common end face. Preferably, the window 5 is hermetically affixed in the fiber tube 4, for instance by soldering, in order that the inside of the optic duct formed by the fiber tube remain vapor-free to protect the optical elements therein.

A system tube 6 is configured in the optic duct subtended by the fiber tube 4 and presents a reduced diameter in its distal end zone 7 where it receives a schematically indicated objective lens 8. A schematically indicated video camera 9 is kept behind said objective lens in the system tube 6 and is connected by conductors 10 to the proximal end segment of the endoscope 1. The video camera 9 looks outward through the objective lens 8 and the window 5.

A heating ring 11 rests against the inner surface of the window 5 and is connected electrically by means of conductors 12 running in the proximal direction. The heating ring 11 may be a wire coil or an electrically resistive annulus. Together with the conductors 10 of the video camera 9, the conductors 12 run in the proximal direction and are connected externally, for instance, to a heating current control. An externally connected temperature sensor controlling the electric heating power also may be used, being configured in the endoscope near the window 5.

A helical spring 13 is configured in the fiber tube 4 and presses by its distal end against the heating ring 11 and by its proximal end against the offset between the system tube 6 and its end zone of reduced diameter. Accordingly, the spring 13 forces a corresponding planar end face of the heating ring 11 against the inner surface of the window 5 in order to assure good thermal contact.

Said spring 13 also might rest against another site within the system tube 6, for instance at its distal end, if for instance the system tube 6 were to end distally absent any dimensional reduction in the end zone 7. Again, this spring 13 might also rest against other components, for instance against an offset of the fiber tube 4. Moreover, the spring 13 might be other than the design shown, illustratively being a cup spring or the like.

In the embodiment shown, the window 5 is firmly soldered into the fiber tube 7. On the other hand, the heating ring 11, the spring 13 and the system tube 6 are displaceable within the fiber tube 4 and may be withdrawn from its proximal end.

In the course of assembly, the heating ring 11, the spring 13 and the system tube 6 are consecutively inserted as a stacked array from the omitted proximal end into the fiber tube 4 until distally stopped. Next, the system tube 6, while loading the compressing spring 13, is advanced a little farther and lastly secured to the endoscope 1, for instance by a screw connection or the like.

The spring 13 not only reliably presses the heating ring 11 against the window 5 in a thermally well conducting manner, but also, by its opposite pressure in the proximal direction, pressed against the system tube 6 to hold it in a play-free manner in the proximal direction. This feature circumvents interfering, clattering motions of the optical system.

In a special embodiment mode, wherein a stack of rod lenses were to replace the shown video camera 9 in the system tube 6, the spring 13 would rest by its proximal end against the stack of rod lenses and in this manner secure their clatter-free support.

The invention claimed is:

1. A medical endoscope (1) comprising an optics duct (4) receiving an optical system (9, 10) enclosed by a system tube (6), the distal end of the optics duct (4) being sealed by a window (5) fitted at its inner surface with an electrical heating ring (11), characterized in that the heating ring (11) rests against the inner surface of the window (5) while being pressed in that direction by a spring (13).

2. Endoscope as claimed in claim 1, characterized in that the spring (13) rests against the system tube (6).

3. Endoscope as claimed in claim 2, characterized in that the heating ring (11), the spring (13) and the system tube (6) are configured in a manner to allow withdrawing them in the proximal direction from the optics duct (4), the system tube (6) resting at its proximal end against the endoscope (1).

* * * * *